United States Patent [19]

Gordon

[11] Patent Number: 5,381,010
[45] Date of Patent: Jan. 10, 1995

[54] PERIODICALLY ALTERNATING PATH AND ALTERNATING WAVELENGTH BRIDGES FOR QUANTITATIVE AND ULTRASENSITIVE MEASUREMENT OF VAPOR CONCENTRATION

[75] Inventor: Eugene I. Gordon, Mountainside, N.J.
[73] Assignee: Sleepair Corporation, Mountainside, N.J.
[21] Appl. No.: 162,443
[22] Filed: Dec. 3, 1993
[51] Int. Cl.⁶ .......................................... G01N 21/61
[52] U.S. Cl. ............................. 250/343; 250/339.13; 250/345
[58] Field of Search ............... 250/343, 345, 350, 351, 250/339.13; 356/437

[56] References Cited

U.S. PATENT DOCUMENTS

| | | | |
|---|---|---|---|
| 3,796,887 | 3/1974 | Vincent et al. | 250/372 |
| 3,807,876 | 4/1974 | Nakahara et al. | 356/437 |
| 3,810,696 | 5/1974 | Hutchins, Jr. | 356/95 |
| 3,904,880 | 9/1975 | Benz et al. | 250/339.13 |
| 3,924,950 | 12/1975 | Siegler, Jr. | 356/95 |
| 3,968,367 | 7/1976 | Berg | 250/343 |
| 3,995,960 | 12/1976 | Fletcher et al. | 250/343 |
| 4,118,625 | 10/1978 | Underwood | 250/343 |
| 4,136,959 | 1/1979 | Honkawa et al. | 356/418 |
| 4,171,909 | 10/1979 | Kramer et al. | 356/435 |
| 4,236,826 | 12/1980 | Yamanishi | 356/432 |
| 4,241,997 | 12/1980 | Chraplyvy | 356/309 |
| 4,305,663 | 12/1981 | Perkins et al. | 356/323 |
| 4,455,097 | 6/1984 | Ichikawa et al. | 356/323 |
| 4,525,627 | 6/1985 | Krempl et al. | 250/339.13 |
| 4,577,105 | 3/1986 | Krempl et al. | 250/343 |
| 4,629,322 | 12/1986 | Pollard | 356/319 |
| 4,637,730 | 1/1987 | Ponstingl et al. | 356/411 |
| 4,750,837 | 6/1988 | Gifford et al. | 356/417 |
| 4,814,604 | 3/1989 | Lequime | 250/227 |
| 4,817,013 | 3/1989 | Corenman et al. | 250/343 |
| 4,856,899 | 8/1989 | Iwaoka et al. | 356/346 |
| 4,899,053 | 2/1990 | Lai et al. | 250/343 |
| 4,921,351 | 5/1990 | Kohigashi et al. | 356/323 |
| 5,055,688 | 10/1991 | Fabinski | 250/343 |
| 5,064,283 | 11/1991 | Tober | 356/73 |
| 5,173,749 | 12/1992 | Tell et al. | 350/343 |
| 5,185,645 | 2/1993 | Sartorius et al. | 356/435 |

OTHER PUBLICATIONS

Article entitled Applications of Single and Multilayer Films, Published in OPTICS, Second Edition, by Eugene Hecht, Adelphi University, Addison-Wesley Publishing Company, pp. 377–378.

Article entitled Near-Infrared Diode Lasers Monitor Molecular Species, by David E. Cooper and Ramon U. Martinelli, Published in Laser Focus World, November 1992 issue, pp. 133–146.

Article entitled Combined Wavelength and Frequency Modulation Spectroscopy: A Novel Diagnostic Tool for Materials Processing, by H. C. Sun, E. A. Whittaker, Y. W. Bae, C. K. Ng, V. Patel, W. H. Tam, S. McGuire, B. Singh, and B. Gallois, published in Applied Optics, 20 Feb. 1993, vol. 32, No. 6, pp. 885–893.

Primary Examiner—Paul M. Dzierzynski
Assistant Examiner—Drew A. Dunn
Attorney, Agent, or Firm—Darby & Darby

[57] ABSTRACT

An apparatus for ultrasensitive detection of low concentrations of constituents using a broad band LED source is described. The apparatus provides enhanced resolution by synchronously detecting an imbalance between two analog signals due to absorption in a measurement cell at a wavelength of interest. Elements are provided to balance the signals in the absence of absorption to provide a reference point for concentration calculations. In accordance with several embodiments of the present invention, a time alternating signal for synchronous detection is achieved by combining signals from each of two alternating paths, only one of which travels through the measurement cell and which may have absorption. If there is absorption in the measurement cell, then the signal created by combining the alternating paths will exhibit residual modulation at the path alternation rate. In accordance with another embodiment of the present invention, a time alternating signal is achieved by combining signals from each of two alternating ultranarrow wavelength channels, each of which travels through the measurement cell but only one of which is on an absorption line of a constituent believed to be in the measurement cell, into a single photosensitive device. If there is absorption in the measurement cell, then the signal from the photosensitive device formed by combining the alternating wavelength channels will exhibit residual modulation at the wavelength channel alternation rate.

36 Claims, 6 Drawing Sheets

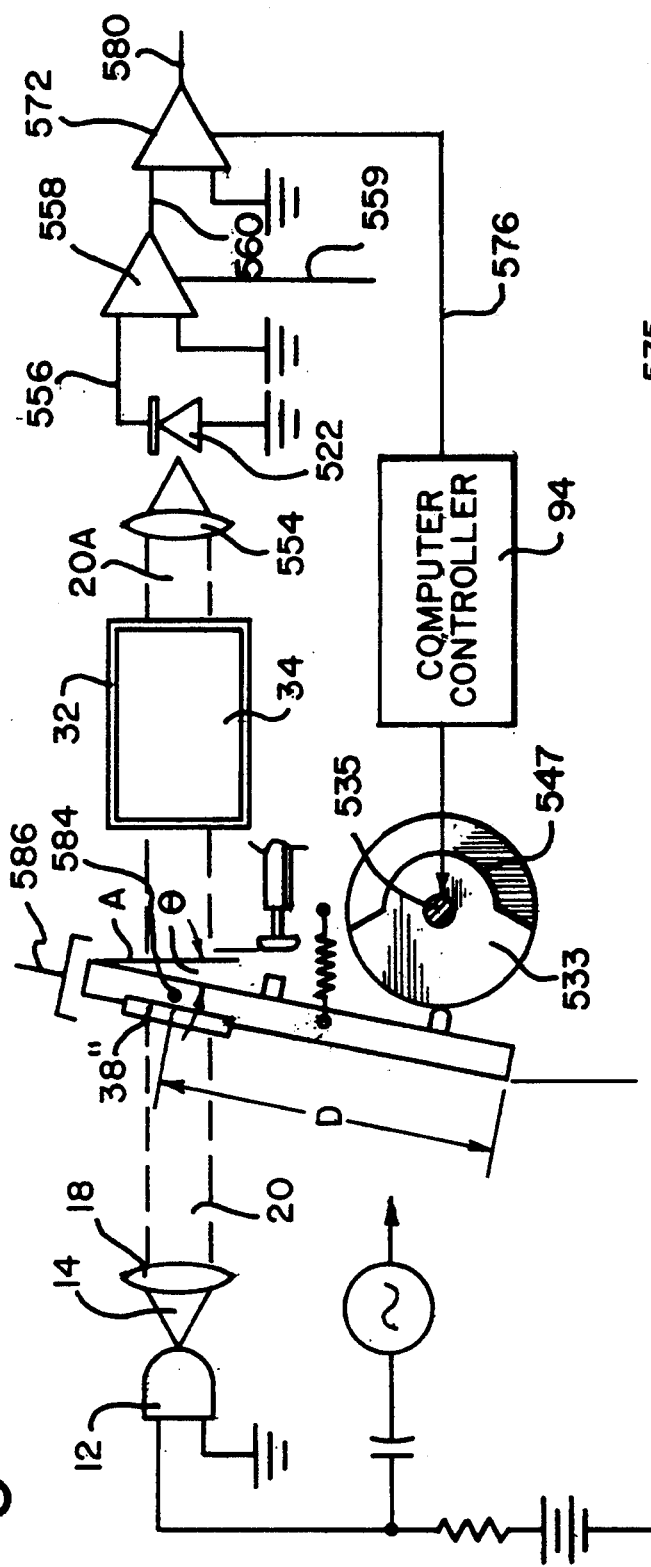
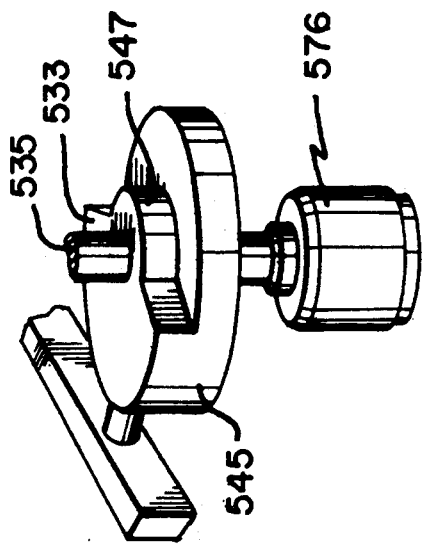
FIG. 5
FIG. 6

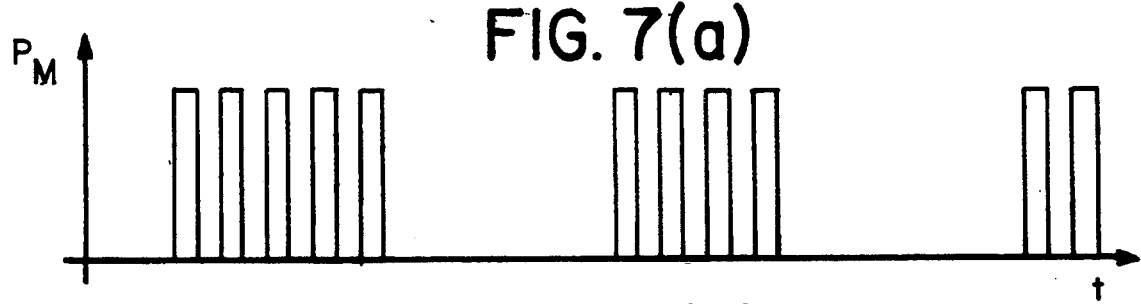
FIG. 7(a)
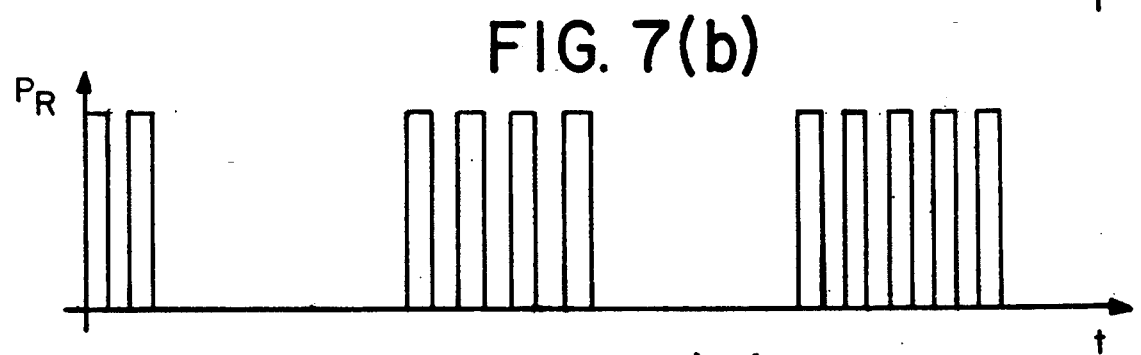
FIG. 7(b)
FIG. 7(c)
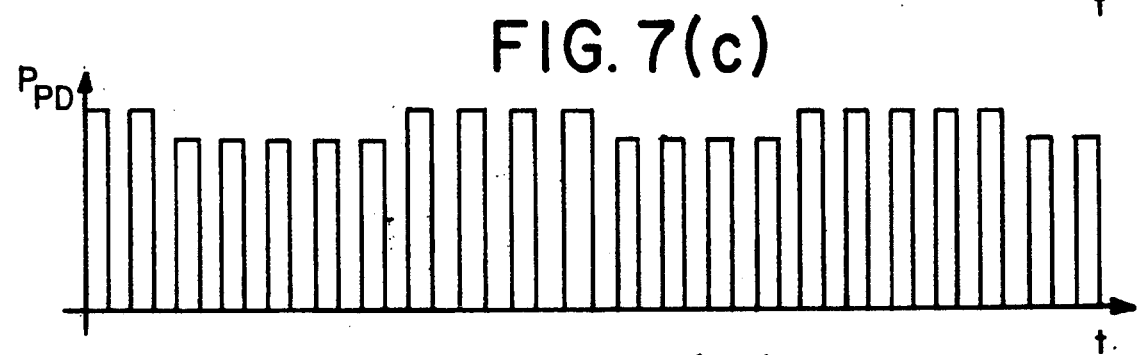
FIG. 7(d)
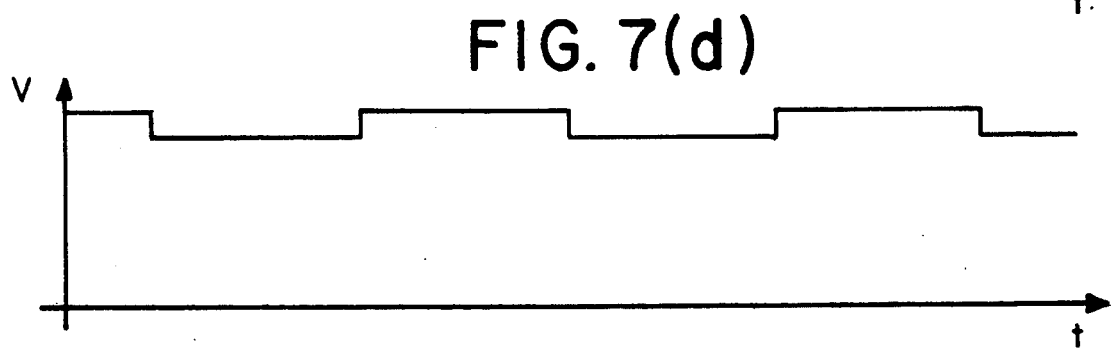
FIG. 7(e)
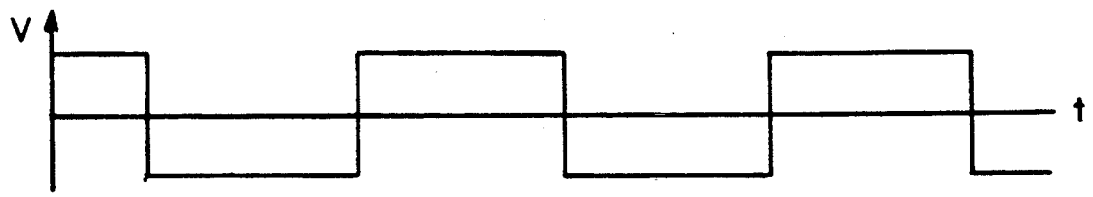

PERIODICALLY ALTERNATING PATH AND ALTERNATING WAVELENGTH BRIDGES FOR QUANTITATIVE AND ULTRASENSITIVE MEASUREMENT OF VAPOR CONCENTRATION

FIELD OF THE INVENTION

The present invention relates in general to spectral absorption monitoring systems and more particularly to a spectrophotometer that is sensitive to ultralow concentrations of constituent molecular gases which uses an incoherent optical source to determine the concentration of a constituent vapor within a volume of gases.

BACKGROUND OF THE INVENTION

Spectral Absorption Monitoring ("SAM") systems operate on the principle that constituent molecular gases within a sample volume of gas have a number of known, narrow absorption lines in the infrared portion of the electromagnetic spectrum. These absorptions lines are associated with transitions from a ground state to a higher energy level of a molecule upon absorption of photons. This higher energy level corresponds to an excited vibrational or rotational state of the molecule. All molecular vapors have absorption lines within the infrared region. Broad band SAM systems are concerned with the determination of the types and quantities of constituent vapors in a sample of gas. Narrow band systems are designed to unambiguously monitor the concentration of a particular vapor. Sensitivity to ultralow concentration and real time measurement are key requirements of narrow band systems, such as the invention described herein.

By transmitting a band of optical energy having a narrow range of wavelengths in and around the peak of an absorption line of a particular constituent, the absorptivity or proportional reduction in transmitted power due to a molecular absorption line of that constituent can be measured to determine its concentration. When this is performed using a measurement cell containing a sample of air of fixed length at a known temperature and pressure, the concentration of the particular constituent believed to be present in the measurement cell can be determined even with very low concentrations. Current sensitive measurement systems have required that the source of spectral output be narrow in wavelength range compared to the half width of the chosen molecular absorption line.

Several constituents may absorb optical energy at the same wavelength. To resolve an ambiguity as to which constituent has what concentration, some absorption systems are chosen to be sensitive to the narrowness of the absorption line, i.e., the absorption signal is proportional to the rate of change of absorption with wavelength. Mathematically, this is expressed as:

$$S_d \propto dA(\lambda)/d\lambda$$

where $S_d$ is the electrical signal detected, A is the absorptivity of the constituent as a function of wavelength, and $\lambda$ is the wavelength. Thus, broad band absorption or scattering within the measurement cell will produce a greatly reduced or possibly no absorption signal because the rate of change of absorptivity with wavelength is negligible. In contrast, the wavelength of the peak absorption of a narrow line is a pretty good signature of a particular constituent. Of course, if a second absorption line of the same constituent vapor is monitored as well a virtually certain signature will be obtained.

Today, narrow band SAM systems tend to be constructed around coherent light sources, typically, single frequency semiconductor laser diodes. Current narrow band spectroscopic research typically utilizes II–VI (lead-salt) semiconductor diode lasers operating in the 3–10 micron spectral region. Such sources are cryogenically cooled and therefore are more expensive and more cumbersome than diode lasers constructed from III–V semiconductor materials such as InGaAsP/InP and GaAs/AlGaAs diodes which operate in the shorter red and near-infrared wavelengths from about 0.63 to 1.55 micron. Nevertheless, the lead-salt laser instruments constructed to date have routinely achieved pans-per-billion (ppb) detection levels of a number of important molecular species. See *Near-Infrared Diode Lasers Monitor Molecular Species,* Laser Focus World, November, 1992, p. 133. The ability to monitor species at ppb levels is of interest to manufacturers of high purity gases used in the semiconductor device fabrication industry where impurities such as $H_2O$ are damaging and reduce the yield of operational circuits. The monitoring of narrow band absorption lines due to water vapor is a particularly useful application of the present invention. Also, air in a workplace or factory can be monitored to meet clean air requirements. Sensitivity to ultralow concentrations has applications in medical diagnostics and in process control.

DISCUSSION OF THE PRIOR ART

The use of a lock-in amplifier to detect alternating pressure differentials due to the absorption of chopped optical energy by the constituents in the test volume is described in U.S. Pat. No. 3,995,960. The '960 method and apparatus relates to spectrophones which measure the concentration of absorbing gases in a sample cell by measuring the alternating component of the pressure by acoustic pressure means. Sensitivity of spectrophone-based systems has suffered due to absorption of the laser source's radiation at the measurement cell's windows which heats the gas near the windows within the measurement cell and registers a false pressure signal. The '960 system instead uses a reflecting light chopper to alternate the paths of a laser output so that a laser beam alternately impinges on a measurement cell at two different locations. Only one of the optical paths has significant optical absorption. With the further use of adjustable attenuators to "zero" the difference in detected pressure in the absence of constituent absorption, as where the laser source is tuned away from the absorption line, the background alternating pressure level can be zeroed to provide enhanced sensitivity for actual absorption measurements. Unless a tunable single frequency laser diode or other substantially monochromatic source is used, the method and apparatus disclosed therein would not be able to discriminate between narrow and broad band absorption lines.

Another sophisticated approach for determining low levels of optical absorption is disclosed in U.S. Pat. No. 5,185,645. By means of a method described therein, a low-frequency fully modulated source is optically split, after transmission through the material being measured, into measurement and reference wavelength channels, respectively, that are in phase. Because each of the measurement and reference channels is fully modulated at the source modulation frequency, a low-frequency lock-in amplifier can simultaneously and synchronously detect the optical power from a photo detector placed in each of these two channels. A difference amplifier then takes the difference between the two synchronously detected wavelength channels in the form of a subtraction. Prior to measurement and in the absence of material that absorbs energy in the wavelength range of the source, the wavelength channels are balanced so that the measurement and reference signals have identical power. The balancing is achieved either by attenuating the stronger of the two light beams or by using a weighting function in the subtraction calculation, as by digital computer.

The method of the '645 patent is an improvement over prior designs that operate by taking the ratio of the detected measurement and reference signals. This is because the resolution of a difference signal is on the order of the magnitude of the imbalance of the signals, rather than being based upon the actual value of the signals which may be several times greater. The method of the '645 patent achieves this improvement by the simultaneous detection of each of the measurement and reference signals and the use of a difference amplifier. The stability of the null according to the method of the '645 patent is limited, however, to the stability of the electrical components, and in particular the photodetectors in each of the reference and measurement paths that generate in-phase signals.

SUMMARY OF THE INVENTION

An object of this invention is to provide an ultrasensitive spectral absorption monitoring system for vapors in an ambient gas or in a vacuum.

A further object is to provide an ultrasensitive spectral absorption monitoring system which uses a stable and relatively inexpensive broad band infrared light emitting diode apparatus as a source.

The present invention provides an ultrasensitive optical absorption monitoring system operable with broad band light emitting diodes that is sensitive to constituent gases in concentrations as low as ppb because concentrations are determined as synchronously detected difference signals with high resolution and, in a preferred embodiment, because the source is amplitude modulated and homodyne detected at high-frequencies outside of the low-frequency noisy region of conventional photosensitive devices. The system comprises a source of broad band infrared radiation, a measurement cell located in a measurement lightpath, another lightpath without the measurement cell for use as a reference, a light chopper that causes the radiation to alternately travel along the measurement lightpath and along the reference lightpath at a first predetermined frequency, variable attenuating elements which permit fine or ultralow increments in relative power in each of the lightpaths for balancing the relative power therein so as to produce a null output signal in the detection system prior to taking measurements, a photosensitive detecting device for detecting an incident optical signal, and a synchronous detection device for extracting a DC signal from the detected incident optical signal which is proportional to absorption due to a concentration of constituent gases in the measurement cell, the absorption being manifested as a residual modulation at the first predetermined frequency. In one preferred embodiment, flicker noise is avoided by means of a modulating device connected to the source so that the IR source output is chopped in time at another predetermined higher frequency, and a demodulating device downstream of the photosensitive device for changing the detected incident optical signal into a low-frequency signal modulated at the alternation rate at the first predetermined frequency before being fed into the synchronous detection device. In another particularly advantageous embodiment, there is a filter positioned ahead of the photosensitive device that passes only an ultranarrow range of wavelengths from each of the lightpaths to the photosensitive device.

While the present invention provides enhanced resolution by measuring an imbalance between the measurement and reference signals in contrast to the method of the '645 patent discussed above, there is only modulation in the synchronously detected analog signal when there is absorption in the measurement cell at the wavelength of interest. While an imbalance in the system will also result in a synchronously detected signal, such imbalance is preferably removed by means of attenuators which insert small amounts of optical loss in the path having greater optical power until both paths have equal power. Thus, the use of a difference amplifier is avoided in several embodiments of the present invention because the synchronous detector detects a time alternating signal proportional to any absorption in the measurement cell only when there is absorption at the wavelength of interest.

In accordance with several embodiments of the present invention, a time alternating signal for synchronous detection is achieved by combining light signals from each of two alternating paths, only one of which travels through the measurement cell and which may have absorption. If there is absorption in the measurement cell, then the signal created by combining the light from the alternating paths will exhibit residual modulation at the path alternation rate. In one embodiment of the present invention, a single wavelength channel with a single photosensitive device can be used to measure narrow band absorption. The use of a single photosensitive device enhances the stability of the null. In accordance with another embodiment of the present invention, a time alternating signal is achieved by combining signals from each of two alternating ultranarrow wavelength channels, each of which travels through the measurement cell but only one of which is on an absorption line of a constituent believed to be in the measurement cell, into a single photosensitive device. If there is absorption in the measurement cell, then the signal from the photosensitive device formed by combining the alternating wavelength channels will exhibit residual modulation at the wavelength channel alternation rate. Again, the use of a single photosensitive device enhances the stability of the null.

Prior designs have typically utilized lasers and other substantially monochromatic sources such as pulsed light emitting diodes, LEDs. The present system may use a high-frequency amplitude modulated broad band LED in combination with a high frequency homodyning circuit to increase the sensitivity of the system so that it is capable of detecting parts per billion concentration of trace constituent gases in a test volume. LEDs afford the advantage that they can be directly amplitude modulated at high frequencies for low noise detection. The only other source that can be directly modulated at high-frequencies is a laser diode. In still another embodiment of the present invention, a high-frequency amplitude modulated source is used in combination with a homodyning circuit to avoid the flicker noise band of conventional photosensitive devices. In this embodiment, a difference amplifier can be used without a synchronous detection circuit because the background noise has been avoided.

The present invention is ideally suited for many specific applications in medical diagnostics and in manufacturing processes and industries where gas analysis is required for process control, cleaner air, or both.

The foregoing and other advantages and features of the present invention will be better understood from the following detailed description when considered in connection with the accompanying drawings.

BRIEF DESCRIPTION OF THE DRAWINGS

FIGS. 1, 2, 3, 4 and 5, respectively, are diagrams of distinct embodiments of a spectrophotometer of the present invention;

FIG. 6 is an enlarged view of the embodiment of FIG. 5 showing the oscillating element in the B position;

FIGS. 7(a), 7(b), 7(c), 7(d) and 7(e) are timing diagrams of the signals propagating through the embodiments of FIGS. 1, 2, 3, and 5.

DEFINITIONS

As used herein, "homodyne detection" and "phase-sensitive detection" refer to detection at relatively high frequencies as compared with "synchronous detection". For example, a homodyne detection circuit used in the present invention might utilize a 10 MHz local oscillator whereas a synchronous detection circuit might utilize a 10 to 2000 Hz reference signal.

In terms of the spectral content or output of the radiation source, the source emits a "wide" or "broad" range of wavelengths in its output band compared to the width of an absorption line.

Absorption lines as discussed herein are to be considered "ultranarrow" compared to the output of the radiation source. Specifically, the term "ultranarrow" as used herein is to be construed as a bandwidth of approximately one nanometer or less, a bandwidth significantly smaller than any reference to "narrow". Preferably, and in accordance with the ordinary meaning of "narrow", the absorption line on which the radiation source output is centered has a sharp, strong energy absorption verses wavelength profile.

"Constituent" or "constituent gases" refers to any atomic or molecular species within a measurement cell whose concentration is to be measured.

"Path" is distinct from "channel" as used in the specification. "Path" refers to a route or direction a beam of light may assume. "Channel" refers to the content of a beam of light as opposed to its direction.

DETAILED DESCRIPTION OF THE PREFERRED EMBODIMENTS

Figure 1:
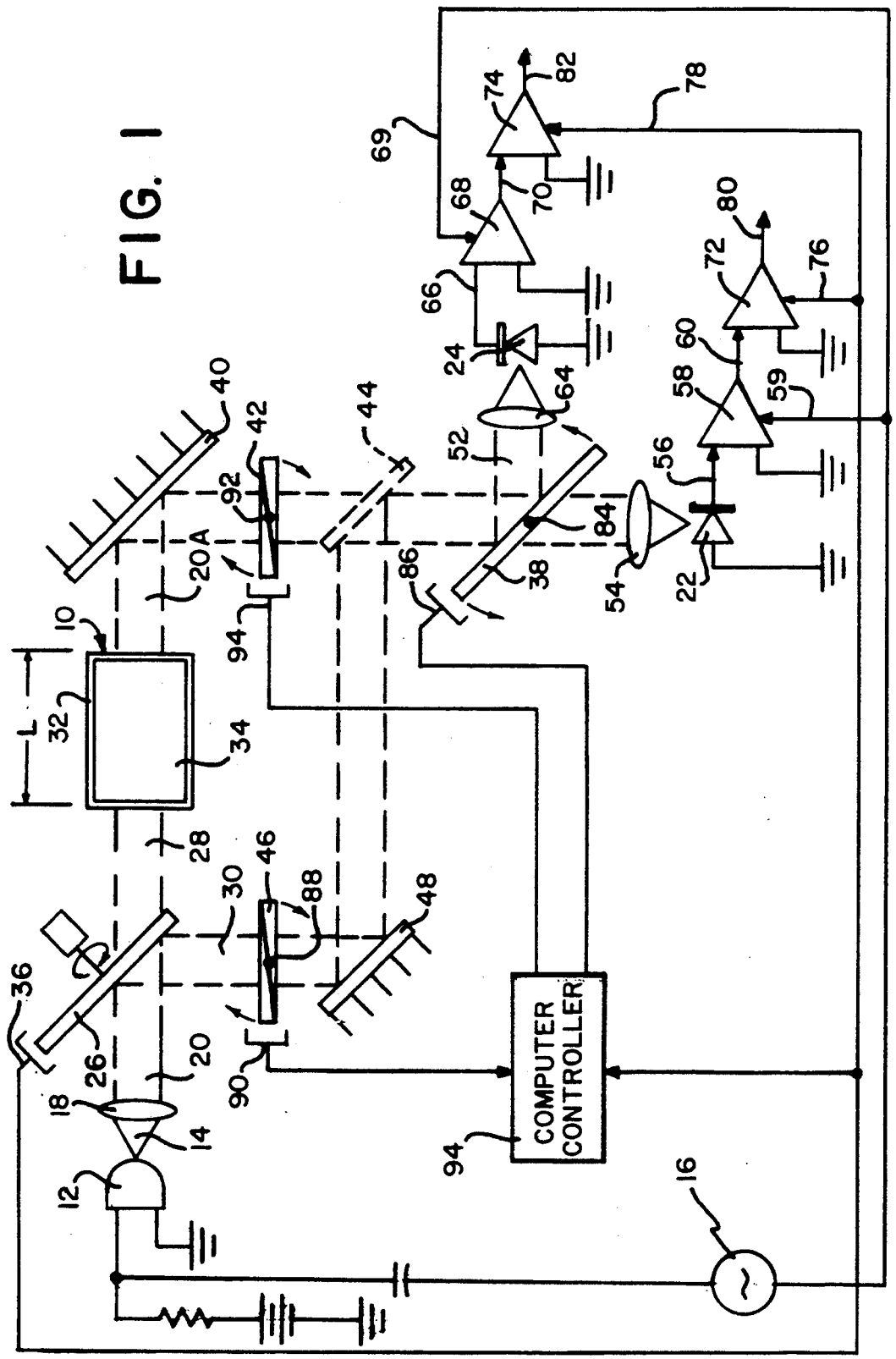

Referring to the drawings, FIG. 1 shows a diagram of one preferred embodiment of a measurement system 10 of the present invention. There, a broad band source 12 produces light 14 that is fully amplitude modulated at a first frequency by a radio-frequency signal generator 16. Modulated light 14 is collimated by a collimator lens 18 into a beam 20 used for measurement and reference purposes in system 10.

Preferably, source 12 is an infrared light emitting diode ("IR-LED"). Source 12 emanates a relatively wide band of electromagnetic energy centered on a particular wavelength, $\lambda_{center}$, which wavelength is temperature dependent and can be thermally "tuned", as described more fully below. The output band of source 12 is wide or broad compared to the width of the absorption line. Such a source usually requires cooling to produce output radiation efficiently or at all. Preferably, generator 16 100% or fully square wave modulates the optical power emanating from source 12 so that the envelope of the transmitted optical light 14 has a DC component from source 12 and a sinusoidal radio-frequency ("RF") component at a given RF frequency, for example, 10 MHz, plus harmonics of the RF frequency from generator 16.

It is seen in FIG. 1 that beam 20 propagates toward photosensitive devices 22,24. Preferably, the photosensitive devices are InGaAs or lead-salt photodiodes or photovoltaic photosensors connected to a voltage source (for diodes) to bias the diodes into their sensitive regions. Beam 20 is first chopped into two time-alternating paths by a motorized rotating chopper or beam deflector 26 to form an optical bridge structure. One path is a measurement path 28 and the other a reference path 30. As illustrated, measurement path 28 contains a measurement cell 32 of length L which may contain a test volume 34 of a gas containing an unknown quantity of constituent. Any absorption will reduce the power of beam 20 at a wave band substantially corresponding to the absorption line of the constituent present, so that beam 20 downstream of measurement cell 32 will have an attenuated power level, denoted as beam 20A. Because reference path 30 does not pass through measurement cell 32, beam 20 has an unattenuated power level therein. Also, because each of paths 28,30 is fully modulated, when the paths are combined at photosensitive devices 22,24, the incremental modulation due to the reduction in power 20A in measurement path 28 can be nulled out. Reference path 30 thus serves to normalize source 12 in the case of beam fluctuations. The labeling of paths 28,30 is, of course, dictated solely by the physical placement of measurement cell 32.

Unlike an interferometer, beam 20 from source 12 does not travel through paths 28,30 at the same time. Rather, beam 20 alternates paths in response to motorized rotating chopper 26 at a pre-determined rate, e.g., 50 Hertz. Standard means to focus beam 20 to a small diameter and then recollimate it are not shown, however, this serves to produce a generally square wave modulated beam. Preferably, chopper 26 is either transmitting the entire beam 20 along measurement path 28 or reflecting the entire beam 20 along reference path 30, at all times. An alternation signal 36 is derived which is responsive to the rotational speed of chopper 26 and in phase with the envelope of the chopped light. The use of rotating choppers to alternate a beam of light is well known in the art. See U.S. Pat. No. 3,796,887. From the foregoing, it should be apparent that chopper 26 causes periodic 100% amplitude modulation signals 180° separated in phase to propagate along the measurement and reference paths 28,30 respectively. These appear as sidebands on the source modulation frequency.

As noted above, chopper 26 either passes or reflects beam 20 in concert with alternation signal 36 as a function of the rotational position of chopper 26. Behind chopper 26, beam 20 travels along measurement path 28 and into measurement cell 32 to exit as beam 20A. Beam 20A is attenuated with respect to beam 20 when there exist constituents that absorb energy within the transmitted spectral band of source 12. Beam 20A is then deviated by a plane mirror 40 so as to pass through an adjustable attenuator 42 and a beam splitter 44 to strike an ultranarrow band pass filter 38, described in detail below. During the time periods that beam 20 is blocked from traveling along measurement path 28, chopper 26 will reflect beam 20 to reference path 30 through an attenuator 46, off of a plane mirror 48 and off of beam splitter 44 so as to strike filter 38 coincidently with beam 20A from measurement path 28.

FIGS. 7(a) and (b) graphically display the temporal relationship between the signals in measurement and reference paths 28, 30, respectively. FIG. 7(a) shows the power of beam 20A downstream of chopper 26 in the measurement path whereas FIG. 7(b) shows the power of beam 20 downstream of chopper 26 in the reference path. The signals in FIGS. 7(a) and (b) are 180° separated in phase. At beam splitter 44, however, these signals are combined so that photosensitive devices 22,24 may produce an output signal having a residual modulation, RM, as shown in FIG. 7(c).

It should be apparent that there will be no residual second frequency amplitude modulation at filter 38 due to the alternation of beam 20 by chopper 26 where paths 28,30 transmit beams of equal power, as where paths 28,30 have been balanced by minutely adjusting attenuators 42,46 so as to insert small amounts of optical loss in the absence of absorption in measurement cell 32. In that case, the amplitude of RM in FIG. 7(c) will be zero. This so called "balanced bridge" condition of the optical bridge formed by 26-28-32-40-42-44 and 26-30-46-48-44, provides a stable null or reference point for determining the concentration of constituents in test volume 34 because there will be no time variation at the second frequency in the optical signal downstream of beam splitter 44 to be synchronously detected. Once a balanced bridge condition is established (with source 12 still being amplitude modulated at a first frequency), extremely small signal differences due to absorption in the measurement path 28 can be synchronously detected by means of alternation signal 36, as described below.

By way of illustration, a parallel plate of optically transparent material is particularly suited for each of attenuators 46 and 42 as a means for introducing small and variable amounts of wavelength insensitive loss. A parallel plate of optical material 46,42 can be inserted into each of paths 28,30, respectively, to introduce a minutely variable amount of insertion loss and thereby independently regulate the power of the beam 20,20A travelling therethrough. A parallel plate of optical material will introduce reflection at each of its two air-material interfaces, one on each side of the plate. The reflectivity of such parallel plate attenuators 46,42 is a function of the angle of incidence of beam 20 or 20A and is readily determined, either empirically or by table data. For low angles of incidence, reflectivity changes slowly with an increase in the angle of incidence. The insertion loss is simply twice the reflectivity and is therefore known absolutely which is important for calibration purposes as discussed below. Preferably, optical plates 46,42 include anti-reflection coatings chosen to have a desired reflectivity verses angle characteristic and to reduce overall transmission loss. It is understood however, that other means for introducing controllable loss are satisfactory for the purpose of balancing the power of the beams in the paths 28,30.

In FIG. 1, beam splitter 44 directs beams 20,20A from paths 30,28, respectively, toward filter 38. Because beam splitter 44 significantly cuts the power of light striking filter 38 which results in a smaller signal at photosensitive devices 22,24, beam splitter 44 could be replaced with a plane mirror 44' (see FIG. 2) so that beam 20 from reference path 30 strikes filter 38 parallel to, but not coincident with, beam 20A from measurement path 28. Plane mirror 44' will not cut the power of beam 20. This is important when source 12 is chosen to be an IR-LED because the maximum spectral output is already lower than that achievable with laser diodes and the use of mirror 44' will therefore maximize power transfer from source 12 to photosensitive devices 22,24.

As previously stated, beams 20,20A from paths 30,28, respectfully, are directed toward filter 38. Filter 38 splits these beams into two separate channels which differ in wavelength yet originate from the common source 12. Any scattering or reflection in the total path due to broad band absorption, smudges or the like will affect both wavelength channels equally because such inadvertent interfering sources are only weakly dependent upon wavelength. Filter 38 has a significant transfer characteristic with regard to the present invention insofar as filter 38 passes only a nanometer band of wavelengths that strike it and filter 38 reflects the remainder of the spectral band. Band pass filter 38 may be of the well known Fabry-Perot transmission spike type. See Hecht, Optics, 2d Ed. p. 377-78. Filter 38 thereby permits discrimination between narrow and broad band absorption using a relatively inexpensive and easy to operate broad band source 12 instead of a sophisticated single frequency laser diode or other substantially monochromatic source. Moreover, by band stopping wavelengths not of interest, filter 38 yields a deeper, more stable null or reference point. This is because other wavelengths may have nulls at attenuator positions very slightly different than $\lambda_{absorption}$ for the gas in test volume 34 which results in a blurring of the null at the wavelength of interest and a reduction in sensitivity to minute absorption.

Filter 38 may comprise two dielectric stacks of quarter wave layers with a separation layer therebetween. The separation layer has a physical thickness, Z, and the stacks each have a reflectivity, R. The separation layer is chosen to have a certain index of refraction, n, and be a multiple, m, of a half wave of a wavelength, $\lambda$, at an angle of incidence of about $\theta = 45°$. This will produce a filter having multiple transmission spikes separated by a wavelength increment, $\Delta\lambda$, defined as:

$$\Delta\lambda = \lambda^2 / 2D$$

where D is the optical thickness ($D = nZ \cos \theta$) and $\lambda$ is the free space wavelength. The width each spike, $\delta\lambda$, is related to the separation of the spikes by the finesse, F, which is determined by the reflectivity and is defined as follows:

$$\delta\lambda = \Delta\lambda / F$$

A typical value of F that can be achieved is 100. Thus, it is possible to observe $$\delta\lambda = \Delta\lambda / 100$$

Accordingly, so long as the spectral output band of source 12 is wider than the width of any spike but less than the wavelength increment between spikes, the multiple spikes can be ignored and only the spike centered on the absorption line will be of interest. The transmission spike constitutes an absorption channel 50 and the reflection constitutes a reference channel 52.

The transfer characteristic of filter 38, noted above, divides the beam incident upon filter 38 into separate wavelength channels 50,52. Each of wavelength channels 50,52 contains the appropriate range of wavelengths for that channel from each of paths 28,30. Absorption channel 50 passes through filter 38 and is focused by a lens 54 upon photosensitive device 22. Because filter 38 has a spatially uniform transfer characteristic and because all light passed through the filter is focused upon the same area of photosensitive device 22, it is not necessary that beams 20,20A from paths 28,30 be coincident.

When filter 38 is properly tuned, as discussed below, one of wavelength channels 50,52 will coincide generally with an absorption line of a particular constituent and that channel will have a power corresponding to the natural power output of source 12 at that ultranarrow band of wavelengths. This is the channel that is passed by the filter 38. The other wavelength channel will reflect from filter 38, in another direction, and will contain the remainder of the spectral output of source 12, namely, two relatively wide bands on either side of the pass band of a generally bell shaped energy distribution curve. In FIG. 1, wavelength channel 50 is the absorption channel and wavelength channel 52 is the reference channel.

With further reference to FIG. 1, it should be apparent that wavelength channels 50,52 traverse similar paths. Thus, absorption channel 50 passes through focusing lens 54 to impinge upon photosensitive device 22. Photosensitive device 22 generates a photocurrent on output line 56 in proportion to the optical power of light in absorption channel 50. The photocurrent, or photovoltage in the case where photosensitive device 22 is chosen to be a photovoltaic device, has the same waveform as the transmitted envelope of beam 20. Preferably, generator 16 generates a square wave signal at 10 MHz, above the flicker noise band of conventional photosensitive devices. In this preferred mode, the photocurrent signal is periodic at the first frequency, that is 10 MHz, and is approximately a square wave, though more precisely trapezoidal in form. The current (or voltage) on output line 56 is proportional to the power of beam 20,20A at the pass band of filter 38. Output line 56 of photosensitive device 22 is connected to the signal input of a homodyne or phase-sensitive detection circuit 58.

The homodyne detection circuit 58 ("HDC") may comprise a mixer having a reference input 59 connected to generator 16 and a signal input connected to the output line 56 of photosensitive device 22. HDC 58 multiplies the input signals and produces a signal at a line 60 whose amplitude is proportional to the product of the input signals from 16 and 22. Because the reference and signal input signals from 16 and 22 are phase synchronized, line 60 will contain a DC signal plus harmonics of the local oscillator signal which are filtered out. Unlike heterodyne detection systems, input signals 16 and 22 are of identical frequency and phase synchronized so the difference frequency of their product is zero thereby producing DC.

A low-pass filter, which is part of HDC 58, passes only the difference frequency, in this case a DC signal, as is well known in the art of phase-sensitive detection. As a result of the homodyne detection of the transmitted optical power, the DC signal on line 60 is derived solely from frequencies in the photocurrent above the low frequency flicker noise output spectrum of conventional photosensitive devices. Accordingly, the combined modulated source 12 and HDC 58 provide more sensitive detection than would be possible if source 12 were unmodulated and the photosensitive device 22 were used directly in its low-frequency, noisy region. Moreover, HDC 58 discriminates against background light that may also impinge upon photosensitive device 22 because unmodulated light will not contribute to the output signal on line 60.

Again with reference to FIG. 1, it is seen that reference channel 52 traverses a similar path to absorption channel 50. Thus, reference channel 52 passes through a focusing lens 64 to impinge upon photosensitive device 24. Photosensitive device 24 generates a photocurrent on an output line 66 in proportion to the optical power of light in the reference channel 52. Again, the photocurrent (or photovoltage) has the same waveform as the transmitted envelope of beam 20 and the current on output line 66 is proportional to the optical power of beam 20,20A outside of the pass band of filter 38. Output line 66 is connected to the signal input of a HDC 68 which also has a reference input 69 that is connected to generator 16 and an output line 70. The signal on output lines 56,66 may approximate that shown in FIG. 7(c) where there is shown a residually modulated signal, having a residual modulation of magnitude RM, due to absorption in the measurement cell or imbalance in paths 28,30.

In operation, the DC signals on lines 60,70 of HDCs 58,68 will exhibit residual modulation at the alternation rate 36 whenever the beams 20,20A in reference and measurement paths 30,28 have differing powers. This is because beams 20,20A in paths 30,28 are 180° separated in phase so as to add constructively at alternation rate 36 to reconstruct the fully modulated beam 20 ahead of chopper 26, at least in the absence of any absorption in measurement cell 32. When the two beams are properly balanced there is no modulation of mixer output signal 58,68 at alternation rate 36. Thus, when paths 28,30 have been previously balanced, any residual modulation is an indication that there is absorption in measurement cell 32, yet this indication is not indicative of the concentration of absorbers in test volume 34 nor does it indicate whether the absorption is narrow in bandwidth and therefore due to a particular constituent as opposed to a relatively broad band line such as nitrous oxide, scattering or the like. This residual modulation previously manifested itself as sidebands of the carrier wave of generator 16, prior to homodyning the sensed signal 56. Where there is residual modulation due to absorption in the measurement cell or imbalance in paths 28,30, the signal on output lines 60,70 may approximate that shown in FIG. 7(d).

The amount and character of the absorption (narrow or broad band) due to this residual modulation is determined by means of a synchronous detector 72 ("SD") in absorption channel 50 and a SD 74 in reference channel 52. SDs 72,74 receive alternation signal 36 at their respective reference inputs 76,78. This signal is shown in FIG. 7(e). SD 72 receives as a signal input line 60 from the homodyne detection circuit 58. SD 72 synchronously detects residual modulation at the ultranarrow range of wavelengths passed by filter 38 after being homodyne detected by HDC 58. SD 72 has on an output line 80 thereof a DC signal in response to that residual modulation, if any, which is proportional to the concentration of constituents in test volume 34 when filter 38 has been tuned (discussed below) to pass an ultranarrow band of waves centered on the absorption line of the constituents being measured.

Either HDCs 58,68 or SDs 72,74 may have a base band filter to integrate their output signals so as to bandwidth limit any noise fluctuations such as "shot" noise that may interfere with the output DC signals. Shot noise will appear at the output of SDs 72,74 as a low amplitude output signal that randomly drifts above and below the zero line with a time constant approximately equal to the integration time. A one second integration time will restrict so called "shot" noise, a random and unavoidable noise fluctuation from photosensitive device 22, to a bandwidth of 1 Hz. Shot noise is described in *Combined Wavelength and Frequency Modulation Spectroscopy: A Novel Diagnostic Tool For Materials Processing*, H. C. Sun et al., Vol. 32, Applied Optics, p.885, 886–87, No. 6, 20 Feb. 1993. A longer integration time will further average the shot noise and reduce the noise fluctuations to a smaller bandwidth (and amplitude), e.g., a ten second integration will reduce the bandwidth to 0.1 Hz. This longer integration time is desirable because it increases the sensitivity of the apparatus and lowers the threshold detectable absorption level, yet longer integration times increase the measurement period and increase the time needed to obtain up-to-date information. Accordingly, a trade-off between measurement speed and shot noise level exists that is resolved as a matter of application specific design criteria. The sign of either SD output signal 80,82 is an indication that one or the other of paths 28,30 has a stronger signal.

The character of the absorption may be determined in two different ways. In the embodiment of FIG. 1, SD 74 receives from line 70 the homodyne detected reference channel signal and synchronously detects any residual modulation from the remainder of the spectral output of source 12, namely, the two relatively wide bands on either side of the pass band of filter 38. SD 74 has on an output line 82 thereof a DC signal in response to the residual modulation, if any, in reference channel 52.

In FIG. 1, the character of the absorption, that is, whether the absorption is narrow or broad band, is determined by taking the difference between the DC output signals 80,82 from the homodyne and then synchronously detected absorption and reference wavelength channels 50,52, respectively. Where both of output signals 80,82 are non-zero, the absorption would be broad band because test volume 34 effects not just the narrow band of wavelengths centered on the absorption line of the constituents in test volume 34, but also the remainder of the spectral output of wide band source 12. In this case, measurement cell 32 can be flushed and refilled with a new test volume 34. If the same result occurs, then there is likely nitrous oxide in the sample or some other undesirable broad band absorber. On the other hand, if output line 80 from absorption channel 50 is non-zero while output line 82 from reference channel 52 is zero, then the absorption would be narrow band within the pass band of the filter and the difference signal, or equivalently the absorption output signal 80 if the measurement proceeded from an initial null reading, would be proportional to the quantity of absorbing constituents in test volume 34. When tuned and balanced, the present invention is capable of ultrasensitive detection of constituents as low as ppb. Another method of determining the character of the absorption is described in connection with FIG. 2.

Sensitivity is heightened when each of filter 38 and the source 12 are fine-tuned, preferably, in that order, and then the system is balanced and calibrated. Fine-tuning is preferably performed by either filling a reference or alignment cell 32' located in reference path 30 or filling measurement cell 32 with a known concentration of constituents.

It is most advantageous to tune filter 38 so that its pass band is centered on the absorption band of a given constituent. Filter 38 is tuned to a particular absorption line by altering the angle of incidence of beam 20A upon filter 38 until a maximum of energy is transferred in a particular wavelength range. This is due to the transmission characteristic of filter 38 which is such that the energy in its pass band varies with the angle of incidence of beam 20A for a fixed wavelength. Thus, filter 38 is suitably oriented when it is in the center of a sharp dip in transmitted energy at the absorption line wavelength, $\lambda_{center}$. As the angle of incidence is altered, the signal in absorption channel 50 will follow the transmitted bell shaped energy distribution curve of beam 20A and exhibit a dip when the angle of incidence corresponds generally with an absorption band of the constituent because energy has been absorbed by the constituents at that wave band. A sharp dip indicates a narrow absorption line. The dip is exhibited as a change in the signal at narrow band output line 80, as well as at lines 56, and 60.

The angle of incidence is altered by mounting filter 38 on a rotatable axis 84 so that the angle of incidence of beam 20A upon filter 38 can be adjusted. A goniometer 64 can be used to precisely rotate filter 38 about axis 84 in increments as small as seconds of arc. The goniometer setting can be stored in a digital computer (not shown) or otherwise registered for recall in case of adjustment.

Source 12 must be tuned to emit wavelengths centered around the transmission characteristic of filter 38. This will maximize the signal in absorption channel 50 by passing the "hump" of the energy distribution from spectral source 12 through filter 38 while concurrently reflecting the sidebands to reference channel 52. Tuning of source 12 is accomplished by minimizing the reference channel signal 82 as a function of the temperature of the source 12 over a small range of temperatures. The LED is thermally tunable by adjusting the ambient temperature, conventionally done by varying current flow in surrounding circuitry (not shown) or by changing the LED's current. When the temperature of source 12 has been adjusted so that absorption channel signal 80 is at a maximum, then source 12 is properly tuned to transmit a maximum energy signal in a range of wavelengths that will pass through filter 38 along absorption channel 50.

The system 10 is balanced by adjusting attenuators 42,46 in the absence of absorption in measurement cell 32. As noted above, there will be no residual modulation at filter 38 and a zero signal at SDs 72,74 when paths 28,30 transmit beams of equal power. Attenuators 42,46 can therefore compensate for non-wavelength dependent signal loss in either of paths 28,30 due to scattering, reflection, imperfections in the optics, or reduction in source power.

Once tuned and balanced, the set-up can be calibrated. Calibration may be achieved by filling measurement cell 32 with a test volume 34 of known concentration so as to constitute an alignment cell 32' for calibration purposes. Alternatively, a cell may be present in reference path 30 for filling with a known concentration to constitute an alignment or reference cell 32'. The signal on output line 80 can be empirically scaled to the known concentration of constituents within alignment cell 32'. The measured absorptivity is given by Beer's law:

$$P(L) = P_o e^{-\alpha L}$$

where $P_o$ is the light power without absorption, $\alpha$ is the absorption coefficient, and L is the length of alignment cell 32'. The absorption coefficient is $$\alpha = CK$$

where C is the concentration of a constituent in alignment cell 32' and K is the calibration constant. The calibration constant for a given experiment can be readily determined where the concentration, measurement cell length, and power in the absence of absorption are known, small products of $\alpha L$, as where there is a low concentration of absorbers, Beer's law can be approximated as $$P(L) \; P_o(1-\alpha L) = P_o - P_o CKL$$

and the calibration constant can be determined by rearranging for K:

$$K = (P_o - P(L))/P_o CL$$

Once the calibration constant is known for a particular absorption line at a particular temperature and pressure for a particular constituent using a source of a certain width, measured absorptivity of test volume 34 in measurement cell 32 can be correlated to the concentration of constituent within the measurement cell 32.

Where attenuators 42,46 are parallel plates of optical material, the absolute insertion loss of these optical elements is determined based on their respective angular positions relative to the direction of beams 20,20A. Because the absolute insertion loss is determinable, the optical bridge of paths 28,30 can be calibrated so that an accurate relationship still exists between the amount of absorption in measurement path 28 to the output of the SDs 72,74. From separate experiments to determine the calibration constant or from data in the literature, the absorptivity of a fixed length of a measurement cell 32 containing a test volume 34 of a constituent at standard pressure and temperature can be related to its concentration. Thus, the DC output of SD 72 can be calibrated directly to the concentration of constituents in a test volume 34, provided the source wavelength is stable. The sensitivity of a synchronous detector based embodiment is limited predominantly by shot noise in the photosensitive device where an amplitude modulated source and a homodyne detection circuit have been used to avoid flicker noise. As noted above, however, shot noise can be significantly reduced by using longer integration times. Reduced shot noise enables measurement of smaller $\alpha L$ products and, in turn, ultralow concentrations of absorbers. The relative shot noise may also be reduced by increasing the output power of source 12.

In operation, a measurement cell 32 filled with a test volume 34 having an unknown quantity of a particular constituent. The constituents within test volume 34 will absorb a narrow band of wavelengths at the wavelength of interest proportional to their concentration. Beam 20A exiting measurement cell 32 will exhibit an energy spectrum, generally, as a bell shaped energy distribution verses wavelength curve with a dip in the distribution in the vicinity of the absorption band of that constituent. This is because the constituents absorb a narrow band of energy from beam 20. This dip in the vicinity of the absorption line will reduce the power of the absorption channel 50, but not the reference channel 52, because absorption channel 50 contains only that ultranarrow band of wavelengths absorbed out of beam 20. The reduction in transmitted power in one channel, but not the other, gives rise to a DC signal at absorption band output line 80 and no signal at reference band output 82. As a result, a signal proportional to the degree of absorption by the constituents in test volume 34 appears at output 80. When the set-up has been properly calibrated, the absorption signal at output 80 can be correlated with empirical or tabular data from cells 32' with known concentration to determine the concentration of constituents within test volume 34. If there were also a DC signal at reference band output 82 after balancing the set-up, as noted above, then the absorption was broad band and measurement cell 32 should be flushed and refilled with a new test volume 34.

Several feedback systems can be included to enhance this and other embodiments described herein. The attenuator means 42,46 for providing very small adjustments to optical loss enables this setup to establish a stable deep broad band null. If there is a difference in the optical power producing the photocurrents, as noted before, some residual modulation will exist in signal 56. This modulation will cause a DC signal to appear at output lines 80,82 of SDs 72,74. The sign of the DC signal on either of output lines 80,82 is determined by which of the measurement or reference paths 28,30 has the greater overall optical transmission loss. Accordingly, an active feedback system can be implemented to examine the sign of the output signals 80,82 to either increase or decrease the insertion loss in one of the paths. Thus, for example, a negative DC signal may indicate that more loss is required in reference path 30 and the feedback system would then adjust the angle of incidence of beam 20 upon attenuator 46 by varying the angle of its axis 88 via a goniometer 90 upon which attenuator 46 is mounted. Similarly, if necessary, attenuator 42 can be rotated on its axis 92 via a goniometer 94. Such a feedback system would better maintain a balance in the optical bridge and thereby reduce the minimum detectable absorption level. The feedback system could be invoked periodically, as by computer 94, to ensure maximum sensitivity.

Source 12 must also be thermally tuned so that it generates a band of energy including the absorption line of the constituents being measured. This too can be automated by a suitable feedback system such as one that uses surrounding circuitry to drive source 12 to higher or lower temperatures until a narrow band absorption signal is detected. This could be accomplished using computer 94 or the like. Such a feedback system serves the important purpose of maintaining the stability of the output wave band of source 12 so that the concentration scale of constituents in test volume 34 remains accurate.

It should be noted that measurement cell 32 may be a gas chamber having a slow flow of a test volume 34 therethrough, or may have a volume 34 of gas sealed therein for testing purposes. Alternatively, a retroreflector can be used to bounce the beam from source 12 across a room and back to photosensitive devices 22,24, so that measurement cell 32 is the space within the room. See, e.g., Laser Focus World, November, 1992, at 144.

In summary, system 10 provides a sensitive response to narrow band absorption exceedingly small concentrations. Because only one source is used, each wavelength channel is identically affected by any fluctuations in power output from the source, any losses in the optical elements due to smudges or imperfections, or any absorption or scattering because such interference is at best weakly dependent upon wavelength. System 10 has a very stable deep broad band null imparted by the alternating paths that contributes to the overall ultrasensitive detection capability. On the other hand, system 10 is also sensitive to narrow band absorption due to the wavelength division of filter 38 and can therefore distinguish narrow from broad band absorption. In combination with a low cost, wide band source, the homodyning circuitry and synchronous detection of transmitted optical power provide an accurate and continuous measurement system.

Figure 2:
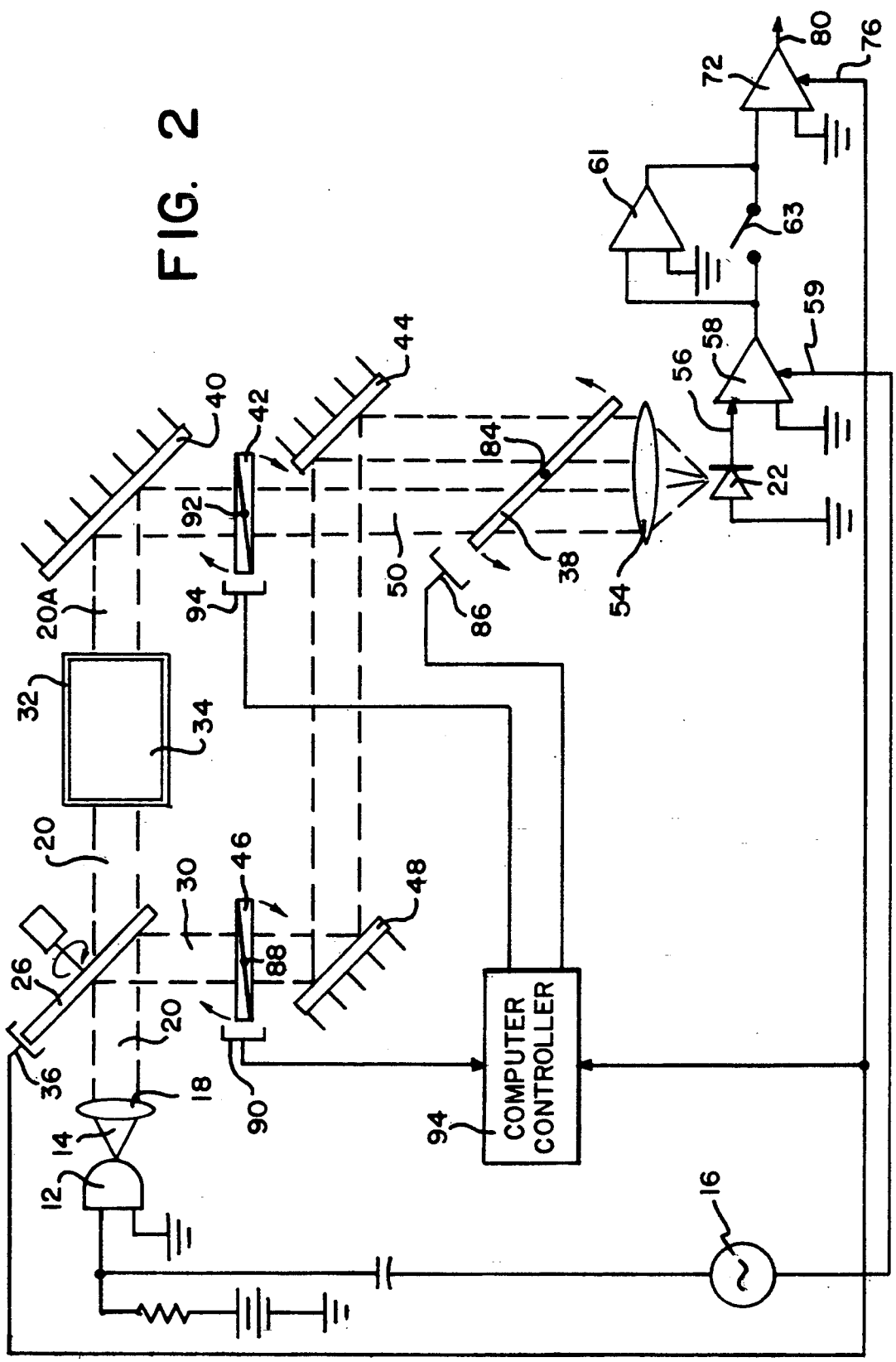

In FIG. 2, there is a diagram of a second embodiment of the present invention having a single wavelength channel, in which features common to the first embodiment are given corresponding reference numerals. Otherwise than as specifically described below, the system of FIG. 2 is essentially the same as in FIG. 1.

With reference to FIGS. 1 and 2, it is seen that FIG. 2 differs from that of FIG. 1 insofar as reference channel 52 and elements associated therewith are absent. Additionally, as discussed above, beam splitter 44 has been replaced by plane mirror 44' to illustrate a journeyman's modification to the embodiment of FIG. 1. Despite the absence of a reference wavelength channel, the embodiment of FIG. 2 provides another method to determine the character of optical absorption (broad or narrow band). While this method is achievable with the above-described embodiment, the reduction in elements in the embodiment of FIG. 2 imparts a distinct cost advantage and reduction in bulk because gone with the reference channel photodetector are the cooling elements and other supporting circuitry (not shown).

Prior to operation, the embodiment of FIG. 2 must be tuned, balanced, and aligned. However, these steps are no different than those already described. Filter 38 is tuned when a signal of maximum power appears at absorption channel output line 80 in the presence of absorbers. The set-up is balanced by zeroing the signal at line 80 through the adjustment of attenuators 42,46. The set-up is calibrated using alignment cell 32' to determine a scale for subsequent measurements of test volumes 34.

In operation, measurement path 28 has a measurement cell 32 is filled with a test volume 34 and a signal proportional to the absorption at the wavelength of interest is detected at output line 80. A single logarithmic circuit 61 may be selectively interposed by switch 63 on line 60 between HDC 58 and SD 72 or after SD 72 (not shown) for synchronous detection of large concentrations of constituent gases in test volume 34. The concentration of absorbers is determined by applying the scale previously determined during calibration.

As distinct from the embodiment of FIG. 1, the character of the absorption can only be determined by detuning the filter to check whether absorption is in fact broad band. This is because there is no reference channel 52 to look to to determine whether the absorption signal is broad band. If the absorption was broad band, varying the angle of filter 38 will have relatively little effect upon signal 80. If the absorption was in fact narrow band, then the signal at line 80 will converge rapidly toward zero as goniometer 86 is adjusted so as to rotate filter 38 about axis 84. This is because the wavelengths passed by filter 38 vary with the angle of incidence upon filter 38 and there would be no absorption at wavelengths alongside an absorption line, unless the absorption was broad band. Subsequent measurements can be taken after retuning filter 38, as by readjusting goniometer 86 to its original position prior to detuning. Goniometer 86 can be adjusted and reset automatically by computer 94. By varying the angle of filter 38, an absorption line profile can be plotted as a function of angle signature.

It should be apparent that filter 38 could readily be located ahead of chopper 26 without impacted the homodyne and synchronously detected signal at line 80.

Figure 3:
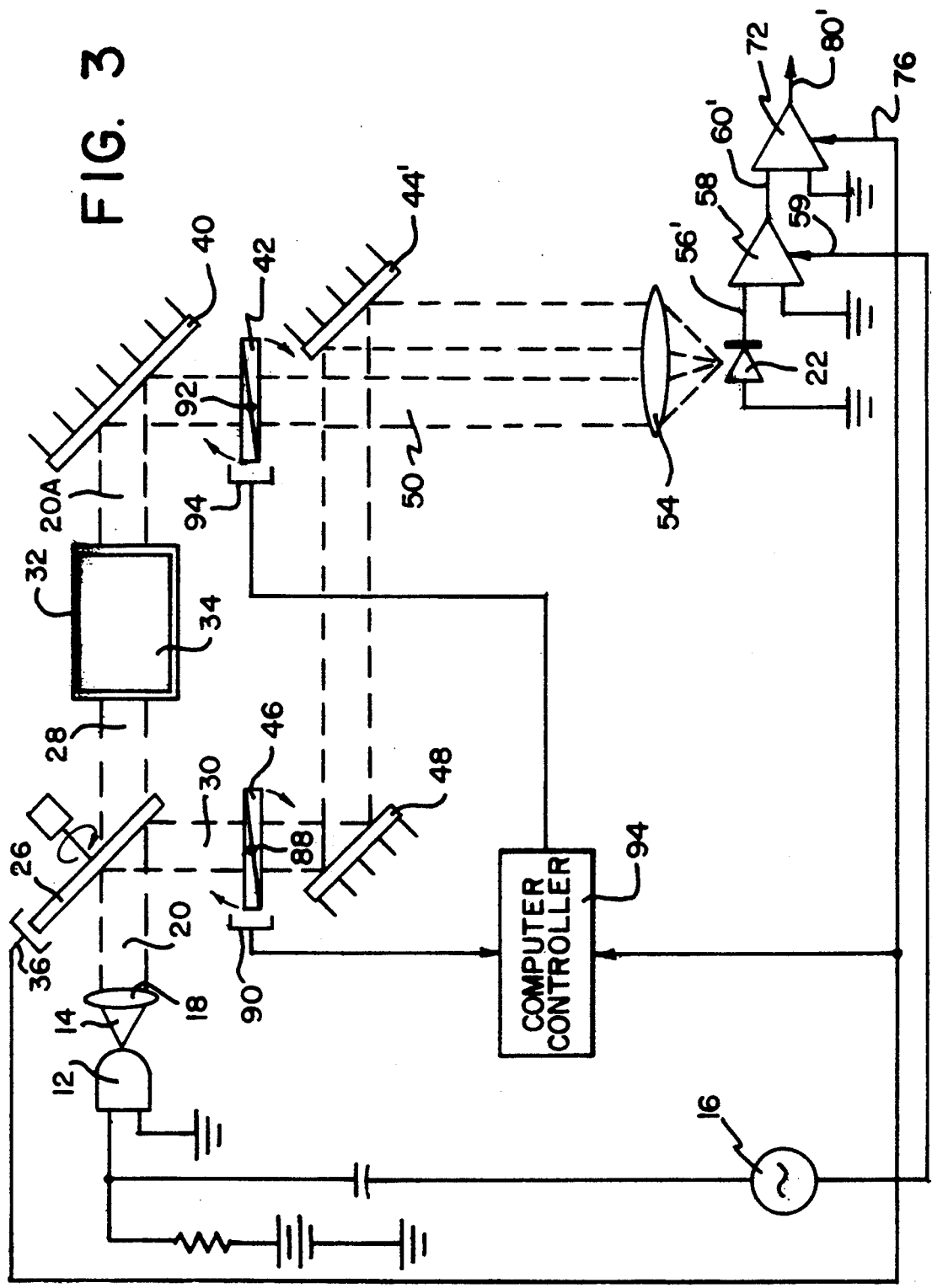

In FIG. 3, there is a diagram of another embodiment of the present invention having no particular wavelength channel, in which features common to the above-discussed embodiments are given corresponding reference numerals. This embodiment, which lacks filter 38, is incapable of verifying that detected absorption is in fact narrow band. Nevertheless, ultrasensitive detection of absorption is available by virtue of the broad and stable null achievable by balancing alternating paths 28,30 using attenuating elements 42,46. Again, generator 16 square wave amplitude modulates the optical power emanating from source 12 so that the envelope of the transmitted optical light 14 has a DC component from source 12 and sinusoidal RF components at a given RF frequency, for example, 10 MHz, and its harmonics from generator 16.

In FIG. 3, plane mirror 44' optically directs beam 20 from reference path 30 toward photosensitive device 22. Plane mirror 44' could be replaced with a separate photosensitive device for the reference channel alone that is electrically connected either in parallel with photosensitive device 22 if the devices generate photocurrent or in series if the devices generate photovoltages.

As in the above-discussed embodiments, the photocurrent (or photovoltage) has the same waveform as the transmitted envelope of beam 20. In this embodiment, however, the signal on output line 56' represents the detected power of the entire spectral output band of source 12, not just an ultranarrow pass band or side bands of the energy output of source 12. Output line 56' of photosensitive device 22 is connected to the signal input of HDC 58.

In the same manner as discussed above, HDC 58 produces a DC output signal at a line 60' whose amplitude is proportional to the product of the signal from generator 16 and the signal from output line 56'. Again, because the reference input and the signal input are phase synchronized, line 60' will be a DC signal. As a result of the homodyne detection of the transmitted optical power, and in accordance with the present invention, the signal on line 60' is derived solely from frequencies above the low frequency noise spectrum of conventional photosensitive devices. Moreover, HDC 58 discriminates against background light that may impinge upon photosensitive device 22 because unmodulated light will not contribute to the output signal on line 60'.

The homodyne detected signal 60' is fed into the signal input of synchronous detector 72 and the alternation signal 36 is fed into the reference port of SD 72 so that the concentration of absorbers in test volume 34 causing any residual modulation can be determined. SD 72 synchronously detects any residual modulation on line 60' as a DC signal on an output line 80' thereof. Unlike the embodiments of FIGS. 1 and 3, line 60' contains the homodyne detected absorption signal for the entire spectral output band of source 12, provided, of course, that source 12 generates a band of energy which includes the absorption line of the constituents being measured.

The embodiment of FIG. 3 requires balancing of the measurement and reference paths 28,30, respectively in order to eliminate residual modulation at the alternation rate 36. This is accomplished by zeroing the DC signal at line 80'. The signal at line 80' has an amplitude (DC value) and a sign (positive or negative). A feedback system of the type described above would be suitable for automating the balancing procedure.

This embodiment is calibrated in the same manner as set forth above. With close control over the wavelength range generated by source 12, this simpler design may be useful in measurements where the presence of absorbers of any kind in a test volume 34 needs to be determined along with their quantity, yet the identity of the absorbers is not relevant. Such a measurement may be, for example, a final stage of a gas purification process to ascertain that a sample of gas is, e.g., six-nines pure (99.9999%).

Figure 4:
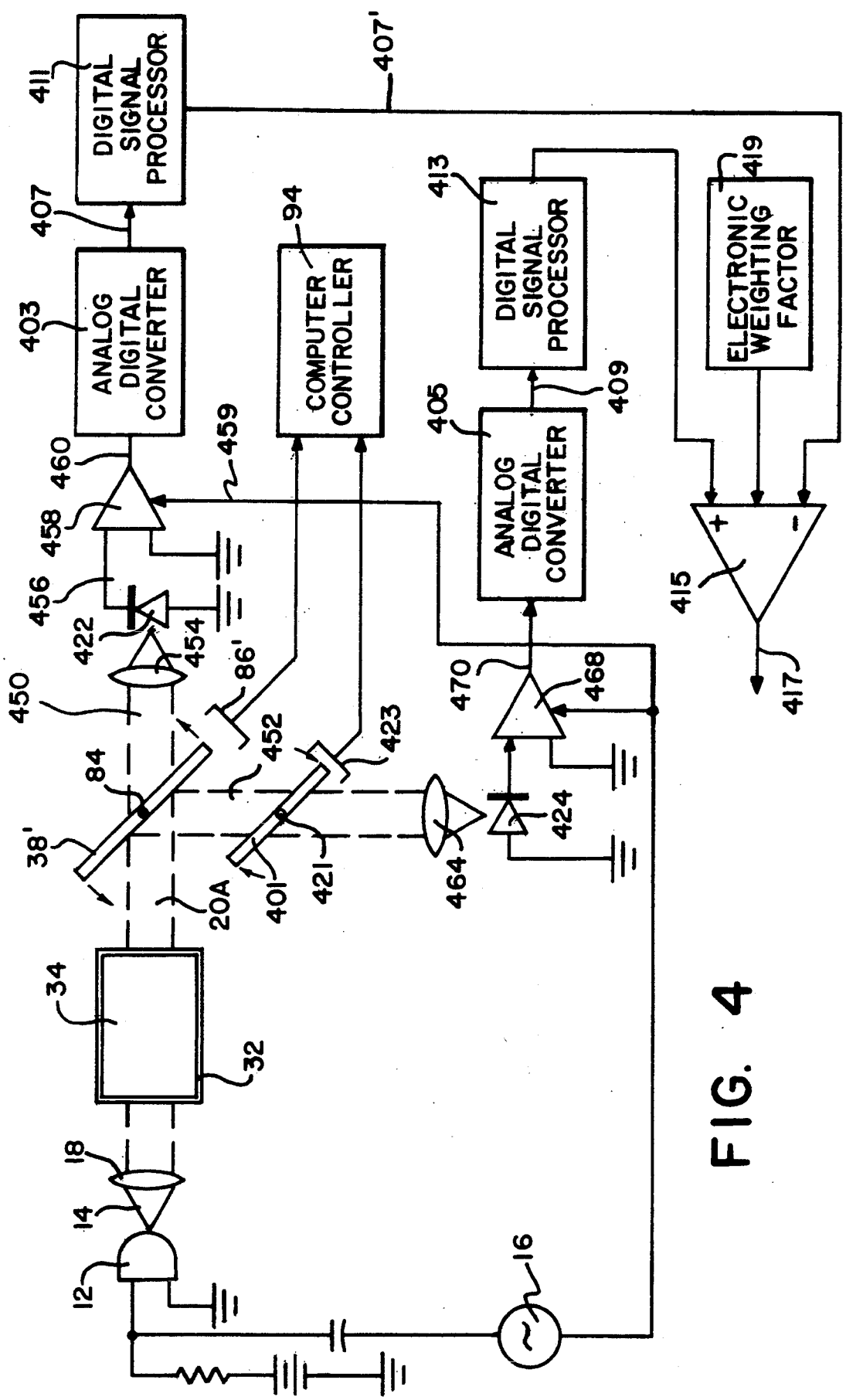

With reference now to FIG. 4, there is seen a diagram of another embodiment of the present invention in which features common to the above-discussed embodiments are given corresponding reference numerals. There, as in the above-described embodiments, a broad band source 12 produces light 14 that is fully amplitude modulated by a radio-frequency signal generator 16. Modulated light 14 is collimated by a collimator lens 18 into a beam 20 that propagates toward photosensitive devices 422,424 for measurement and reference purposes.

Beam 20 passes directly through a measurement cell 432 before being split into, distinct wavelength channels 450,452 by an ultranarrow band filter 38'. Beam exits measurement cell 432 as beam 20A which will have been attenuated with respect to the power of beam 20 if there were absorbers within a test volume 434 in the range of wavelengths generated by source 12. Filter 38' has the same properties as filter 38, described above, and may be formed in the same way. Thus, in FIG. 4, absorption channel 450 is passed through filter 38' and measurement channel 452 is reflected off of filter 38'.

As in FIG. 1, absorption and measurement channels 450,452 traverse similar paths. Thus, absorption channel 450 passes through focusing lens 454 to impinge upon photosensitive device 422. Photosensitive device 422 generates a photocurrent (or photovoltage) on output line 456 in proportion to the power of light in absorption channel 450. The photocurrent (or photovoltage) has the same waveform as the transmitted envelope of beam 20. Preferably, generator 16 generates a square wave signal at 10 MHz, above the noise band of conventional photosensitive devices. In this preferred mode, the photocurrent signal, is periodic and is approximately a square wave, though more precisely trapezoidal in form. The current (or voltage) on output line 456 is proportional to the power of beam 20A at the pass band of filter 38'. Output line 456 of photosensitive device 422 is connected to the signal input of a HDC 458.

The HDC 458 may comprise a mixer having a local oscillator input 459 connected to generator 16 and a signal input connected to the output line 456 of photosensitive device 422. HDC 458 multiplies the input signals and baseband filters the output signal to produce a DC output signal at a line 460 whose amplitude is proportional to the product of the input signals from 16 and 422. Because the local oscillator and signal input signals from 16 and 422 are phase synchronized, line 460 will be a DC signal. Unlike heterodyne detection systems, input signals 16 and 422 are of identical frequency and so the difference frequency of their product is zero.

A base band filter, which is part of HDC 458, passes only the difference frequency, in this case a DC signal, as is well known in the art of phase-sensitive detection. As a result of the homodyne detection of the transmitted optical power, the DC signal on line 460 is derived solely from frequencies above the low frequency flicker noise spectrum of conventional photosensitive devices. Accordingly, the combined modulated source 12 and HDC 458 provide more sensitive detection than would be possible if source 12 were unmodulated and the photosensitive device 422 were used directly in its low-frequency, noisy region. Moreover, HDC 458 discriminates against background light that may also impinge upon photosensitive device 422 because unmodulated light will not contribute to the output signal on line 460.

As described above, HDCs 458,468 have a base band filter to integrate their output signals so as to bandwidth limit any "shot" noise that may interfere with the output DC signals.

Again with reference to FIG. 4, it is seen that reference channel 452 traverses a similar path to absorption channel 450. The beam 20A in reference channel 452 first passes through an optical attenuator 401. Optical attenuator 401 allows attenuation of the reference channel 452 power for balancing the system, discussed more fully below. Next, beam 20A passes through a focusing lens 464 to impinge upon photosensitive device 424. Photosensitive device 424 generates a photocurrent on an output line 466 in proportion to the power of light in the reference channel 452. Again, the photocurrent (or photovoltage) has the same waveform as the transmitted envelope of beam 20 and the current on output line 466 is proportional to the power of beam 20A outside of the pass band of filter 38'. Output line 466 is connected to the signal input of a HDC 468 which also has a local oscillator input 469 that is connected to generator 16 and an output line 470.

The signals 460,470 from HDC 458,468 are respectively converted to digital signals by analog-to-digital convertors 403,405 ("ADC"). Convertors 403,405 respectively provide a digital signal on lines 407,409 representative of analog signals 460,470. These signals may be fed to digital signal processors 411,413 ("DSPs"), respectively, for further noise reduction and processing. If processed, signals 407,409 exit DSPs 411,413 as 407',409', respectively. This further processing assists in achieving a better reference level or "zero" for measuring absorption in measurement cell 20. ADCs 403,405 may comprise conventional sixteen bit convertors having 65,536 output levels. Such convertors would correspond to a system capable of registering changes in absorption, αL, of approximately one and a half parts in 100,000. By Beer's law, stated above, this corresponds to a resolution of concentration of a constituent within a measurement cell of gas of up to fifteen parts per billion, depending upon the exact value of the calibration constant.

Digital signals 407′,409′, whether further processed by a digital processor or not, are fed to differential inputs of differential amplifier 415. Differential amplifier 415 subtracts one of signals 407′,409′ from the other and has on its output line 417 a DC signal indicative of absorption or imbalance in wavelength channels 450,452. As shown in FIG. 4, digital signal 407′, which is representative of absorption channel 450, is subtracted from digital signal 409′, which is representative of reference channel 452. If wavelength channels 450,452 had been balanced and the set-up aligned, then output line 417 would have a signal proportional to the absorptivity of the test volume 434 in measurement cell 432, sensitive to one part in 65,536, where a sixteen bit converter is used. Convertors having greater numbers of bits will result in a system having greater sensitivity to still lower concentrations of a constituent, limited only by the stability of the null reference point.

In order to realize meaningful results, the dual channel set-up of FIG. 4 must be fine-tuned, balanced, and calibrated prior to performing the above measurement. Tuning and calibration are accomplished as described in connection with FIG. 1. To balance wavelength channels 450,452, it is preferable, but not required, that output line 417 from digital differential amplifier 415 indicate a zero differential between measurement and reference channels 450,452, in the absence of absorption in test volume 34. However, all that is required is that the channel differential be known and constant during subsequent measurements.

It is greatly preferred that the differential between reference channel 452 and measurement channel 450 be set to zero in the absence of absorption. In order to zero or "null" the channel differential to get a zero output on output line 417, the power of beam 20A on wavelength channels 450,452 must be balanced. One way in which the differential can be brought to zero is by inserting optical attenuator 401 in reference channel 452 for attenuating the power of beam 20A impinging upon photodetector 424 which in turn reduces the digital signal 409′ received as an input to differential amplifier 415 until output line 417 indicates zero. Attenuator 401 may comprise one or more neutral density filters. Attenuator 401 may be rotated upon an axis 421 under the control of a goniometer 423, in similar fashion to attenuators 42,46 discussed above. Another manner in which the differential can be brought to zero is by applying an electronic weighting factor 419 to differential amplifier 417. Factor 419 can be programmed to offset an output signal at output line 417, as by a switch-in, switch-out feedback loop from output 417 to a selectively inverting input of differential amplifier 415. This is known as a "balanced" condition because the homodyne detected power in each of measurement and reference channels 450,452 is identical.

A measurement cell 432 containing an unknown quantity of constituents in test volume 434 need not be removed in order to balance the system in FIG. 4. Instead, filter 38′ can be rotated on axis 84′ so that the transmission characteristic is no longer sensitive to the absorption line of the constituents in measurement cell 432. Because the wavelengths passed by filter 38′ vary, with their angle of incidence, filter 38′ can be rotated so that each of paths 450,452 receives wavelengths separated from an absorption line of the constituents in measurement cell 432. Subsequent measurements can be taken after retuning filter 38′, as by readjusting goniometer 86′ to its original position prior to detuning. Goniometer 86′ can be adjusted and reset automatically by computer 94. Alternatively, source 12 can be thermally tuned to emit wavelengths separated from an absorption line of the constituents in measurement cell 432 and retuned after wavelength channels 450,452 are balanced.

As a result the dual channel system of FIG. 4 provides sensitive response to small narrow band absorptions. Because wavelength channels 450,452 traverse the same optical path, each channel is identically affected by non-wavelength dependant interferences such as fluctuations in power output from the LED, losses in the optical elements due to smudges or imperfections, or absorption or scattering in the path between source 12 and photosensitive devices 422,424. The embodiment of FIG. 4 may require periodic rebalancing due to microdrifting as the ambient temperature changes which may be accomplished automatically by a feedback network of the type described in connection with FIG. 1.

In FIGS. 5 and 6, there is a diagram of yet another embodiment of the present invention in which features common to the above-discussed embodiments are given corresponding reference numerals. This embodiment features alternating wavelength channels A and B and a single lightpath. The distinguishing characteristic of this embodiment is the mount for filter 38″ which is designed to alternate filter 38″ periodically through two transmission wavelengths by rapidly changing, e.g., 60 Hz, the angle of incidence of beam 20 upon filter 38″. FIG. 5 illustrates an apparatus suitable for this purpose.

Filter 38″ is shown to be mounted upon an oscillating element 525. Oscillating element 525 ("OE" 525) has a length D and a width W and pivots about a point 584. OE 525 has an A position 529 and a B position 531 corresponding to wavelength channels A and B, respectively. In FIG. 5, OE 525 is in position B which orients filter 38″ at an angle $\theta$ with respect to beam 20. OE 525 is driven between positions 529, 531 by a motorized circular rotating cam 533, shown in detail in FIG. 6. Cam 533 rotates about an axis 535. In A position 529, filter 38″ has been pivoted $\Delta\theta$ with respect to beam 20 so that the angle of incidence of beam 20 upon filter 38″ has changed from $\theta$ to $\theta + \Delta\theta$. The change in angle, $\Delta\theta$, is $$\Delta\theta = W/D$$

As cam 533 rotates, OE 525 will cause filter 38″ to periodically and alternatingly pivot $\Delta\theta$ degrees with respect to an angle $\theta$. OE 525 need only move a few microns to oscillate between positions A and B. Accordingly, very little force is required to move OE 525, especially where filter 38″ and OE 525 are made of light weight material. The period of oscillation is the rotation period of cam 533. Since the peak transmission of the filter is at a wavelength $\lambda$ such that $$((2\pi n/\lambda_m) \cos \theta)Z = m\pi$$

the peak transmission at positions A and B, respectively are $$\lambda_A = (2nZ/m)\cos\theta_A$$

$$\lambda_B = (2nZ/m)\cos\theta_B$$

where Z is the physical thickness of filter 38'' and m is an integer. Accordingly, as filter 38'' alternates between positions A and B, the transmitted wavelength will alternate between $\lambda_A$ and $\lambda_B$ with the rotation period of cam 533. Source 12 is chosen to have a spectral output that at least encompasses $\lambda_A$ and $\lambda_B$. Unlike coherent systems using a frequency modulated single frequency laser source, source 12 of the present embodiment produces large wavelength differences. Thus, once beam 20 reaches measurement cell 32 downstream of OE 525, beam 20 will periodically and alternately have energy at $\lambda_A$ and then at $\lambda_B$, will be seen that at $\theta_A = 45°$, $$\Delta\lambda \quad \lambda_A - \lambda_B = \lambda_A (W/D)$$

A minimum desired value for $\Delta\lambda$ is about five nanometers. Because W and D can be chosen so that W/D is about $10^{-5}$, as where W is one micron and D is 10 cm, the desired $\Delta\lambda$ can be achieved for wavelengths of 3,000 to 10,000 nanometers. Thus, OE 525 provides periodic and alternating wavelengths for precise absorption measurements, as described below.

OE 525 has on a rear surface 537 a stop 539 having a protuberance 541 at a distal end 543 thereof which periodically and selectively engages a camming surface 545 of cam 533 as cam 533 rotates about axis 535. When protuberance 541 engages camming surface 545, OE 525 is cammed to the B position 531 against the restoring force of a spring 549. When camming surface 545 is not engaged with protuberance 541, OE 525 pivots in the direction of arrow A in response to the restoring force of spring 549. OE 525 will continue to pivot until a stub 551 on rear surface 537 contacts a stopper 553, at which time OE 525 has reached the A position 529. Cam 533 is preferably formed with a radially recessed surface 547 which does not contact protuberance 541 so that measurements of the absorption line can be taken while OE 525 is not in contact with or affected by any eccentricities of rotating cam 533. B position 531 may also be used for taking measurements, but is not the preferred measurement position. Preferably, camming surface 545 is formed so that OE 525 remains in each of positions 529, 531 for an equal amount of time which approximates half of the rotation period of cam 533.

In operation, a polychromatic beam 20 passes through filter 38'' which, as a function of angular with respect to beam 20, alternately and periodically divides beam 20 into one of two wavelength channels. Each of these wavelength channels then passes through measurement cell 32 which may contain a test volume 34 and exits cell 32 as a beam 20A. This beam is passed through a focusing lens 554 to impinge upon a photosensitive device 522. If source 20 was amplitude modulated by a generator 16, as in the previously described embodiments, then a homodyning and base band filter circuit would homodyne the signal on an output line 556 of photosensitive device 522, using the output of generator 16 as a local oscillator input 559 to a homodyning circuit 558. When present, the homodyning circuit produces a D.C. signal on line 560 which may exhibit residual amplitude modulation due to absorbers in test volume 34 or an imbalance in the power in the two wavelength channels. This residual modulation is extracted by a synchronous detection device 572 which has as a reference signal 576 the rotation period of cam 533 in phase with position A or B. When there is no homodyning circuit, the photosensitive device output is fed as a signal input to the synchronous detector.

In the embodiment of FIG. 5, source 12 is tuned roughly on the chosen absorption line wavelength, as in the previous embodiments. Unlike the previous embodiments, however, source 12 is thermally tuned over a small range of temperatures until the output spectrum of source 12 has equal energy at each of $\lambda_A$ and $\lambda_B$, in the absence of absorption at either one of the wavelengths. By balancing the energy at each of $\lambda_A$ and $\lambda_B$, the synchronous detection device 572 will produce a null or zero output on line 580 because the alternating wavelength bridge formed by oscillating element 525 and rotating cam 533 will show no time variation of the photodetected optical power and there will be no signal to detect.

In the event of broad band absorption, both of channels A and B will experience a reduction in detected power in identical proportion. Accordingly, the balance of the alternating wavelength bridge will be preserved.

To detect narrow band absorption, oscillating element 525 is rotated about point 584 by means of a goniometer 586 to "tune" filter filter 38''. Whereas cam 533 is used to drive filter 38'' through $\Delta\theta$, goniometer 586 adjusts $\theta$, the base angle from which filter 38'' oscillates. While goniometer 586 is being adjusted, cam 533 continues to rotate and filter 38''' continues to alternately and periodically pass two wavelength channels separated in wavelength by $\Delta\lambda$. So long as goniometer 586 is being adjusted, the wavelength being transmitted through filter 38'' at each of $\lambda_A$ and $\lambda_B$ will also be changing. Filter 38'' is tuned, and a measurement is performed, by varying $\theta$ until one of $\lambda_A$ and $\lambda_B$, and preferably $\lambda_A$, corresponds with a narrow absorption line of a constituent under test.

Assuming, for example, that $\lambda_A$ and $\lambda_B$ are to the left of an absorption line of interest, that is $$\lambda_{absorption} > \lambda_A, \lambda_B$$

neither of the wavelength channels will experience absorption and a null signal will result at output 580 of the balanced alternating wavelength channel setup. As $\theta$ is increased by adjusting goniometer 586, $\lambda_A$ and $\lambda_B$ move rightward toward $\lambda_{absorption}$. When $\lambda_B$ overlaps $\lambda_{absorption}$, there will be absorption only in channel B and the bridge will unbalance thereby producing an output signal at line 580 proportional to the amount of absorption in test volume 34. The sign of the signal at line 580 (positive or negative) is a function of the phase of the reference signal from the motor of cam 533. Further adjustment of goniometer 586 will tune filter 38'' so that $\lambda_A$ and $\lambda_B$ straddle the absorption line, assuming $\Delta\lambda$ is greater than the width of the absorption line. There will be some $\theta$ at which there is again a balance in $\lambda_A$ and $\lambda_B$ such that the bridge is once again balanced. Still further adjustment of goniometer 586 will cause $\lambda_A$, the preferred measurement channel, to coincide wills $\lambda_{absorption}$. The bridge will again be unbalanced and produce a similar value output signal at line 580 proportional to the amount of absorption in test volume 34 but of opposite sign of that obtained when channel B overlapped $\lambda_{absorption}$. This signal may be more reliable because in A position 529, oscillating element 525 is disengaged from rotating cam 533 which could otherwise impart noise or blur the measurement.

The magnitude of $\Delta\theta$ is controlled by a vernier drive 555. Vernier drive 555 positions stopper 553 with respect to stub 551. The absolute location of stopper 553 determines the A position 529 and therefore the degree of pivotal motion of OE 525 between $\theta$ and $\theta \pm \Delta\theta$.

Before a measurement is made, the setup must also be calibrated. A test volume 34 of known concentration is introduced into measurement cell 32' and a plot of output signal on line 580 verses $\theta$ is produced until one of $\lambda_A$ and $\lambda_B$, preferably $\lambda_A$, is tuned to coincide with $\lambda_{absorption}$, in the manner discussed above. Goniometer 586 is then locked in place so that $\theta$ remains constant during the measurement and filter 38" alternately and periodically varies in angle only by $\Delta\theta$. This position is preferably stored or noted, as by computer controller 94 for later retrieval or reference. The value of signal 580 is then calibrated to a known or empirically determined scale. Source 12 is then thermally tuned again in the absence of absorbers to produce a balanced or zero output at line 580. Source 12 can be periodically retuned to ensure the stability of the null in subsequent measurements.

With a test volume of gas 34 in measurement cell 32, $\theta$ may be tuned so that the absorption signature of test volume 34, that is, the profile of the absorption as a function of wavelength, can be observed. This may be plotted to a peripheral device (not shown) attached to output line 580 and perhaps computer controller 94. As in each of the above-discussed embodiments of the present invention, if the absorption half width is narrow compared to the filter half width, the signature will correspond to the filter transmission characteristic.

All, or substantially all, of the components and methods of the various embodiments may be used with at least one embodiment or all of the embodiments, if any, described herein. It should be noted that chopper or deflector 26 could be a galvanometer. Also, generator 16 could be configured so as to modulate the power supply coupled to source 12 (not shown) or could take the form of an electro-, acousto- or magneto-optic modulator.

All of the patents, patent applications, publications, and chapter sections recited herein are hereby incorporated by reference as if set forth in their entirety herein.

From the foregoing description, it will be clear that the present invention may be embodied in other specific forms without departing from the spirit or essential characteristics thereof. Thus, for example, while the present invention is able to discern extremely low concentrations of constituent gases, it is likewise useful for measuring large absorption signals. Likewise, while beam splitter 44 and plane mirror 44' have been depicted and described as separate, free-standing elements, they can be integrally housed along with any of photosensitive devices 22,24,422,424. The presently disclosed embodiments are therefore to be considered in all respects as illustrative and not restrictive, the scope of the invention being indicated by the appended claims, and not limited to the foregoing description.

I claim:

1. An apparatus for measuring optical absorption by a constituent gas in a measurement cell, said apparatus comprising:
    radiation means for emitting broad band infrared radiation along one of a measurement lightpath and a reference lightpath, the measurement cell being positioned in said measurement lightpath so that said radiation passes therethrough;
    alternating means for alternately and periodically directing said radiation along one of said lightpaths at a first frequency;
    attenuating means for balancing the relative power of said radiation in each of said lightpaths in the absence of optical absorption of the constituent in the measurement cell:
    sensor means for sensing radiation from each of said lightpaths and for producing a sensed signal, said sensed signal exhibiting modulation thereupon at said first frequency only when there is optical absorption of the constituent in the measurement cell; and
    synchronous detection means for demodulating said first frequency from said sensed signal so as to extract a DC signal, said DC signal being proportional to the optical absorption of the constituent in the measurement cell.

2. An apparatus as in claim 1 further including modulating means for modulating said emitted radiation at a second frequency so that said radiation in each of said alternating lightpaths is modulated, and demodulating means connected between said sensor means and said synchronous detection means for demodulating said second frequency from said sensed signal.

3. An apparatus as in claim 2 wherein said second frequency is higher than said first frequency and further chosen to be above a flicker noise region of said sensor means.

4. An apparatus as in claim 1 further comprising calibration or calculation means for relating said DC signal from said synchronous detection means to the concentration of the constituent in the measurement cell.

5. An apparatus as in claim 1 further comprising means for thermally tuning said radiation means so that said radiation means emits a band of radiation centered on an absorption line of the constituent in the measurement cell.

6. An apparatus as in claim 1 wherein said detected signal also exhibits residual modulation when there is an imbalance in the relative power from said radiation means traversing said lightpaths, and said DC signal is an indication of said imbalance in the absence of optical absorption of the constituent in the measurement cell.

7. An apparatus for measuring optical absorption by a constituent gas in a measurement cell, said apparatus comprising:
    radiation means for emitting broad band infrared radiation along one of a measurement lightpath and a reference lightpath, the measurement cell being positioned in said measurement lightpath so that said radiation passes therethrough;
    modulating means for modulating said emitted radiation at a first frequency;
    alternating means for alternately and periodically directing said radiation along one of said lightpaths at a second frequency;
    attenuating means for balancing the relative power of said radiation in each of said lightpaths in the absence of optical absorption of the constituent in the measurement cell:
    sensor means for sensing radiation from each of said lightpaths and for producing a sensed signal;
    demodulating means for demodulating said first frequency from said sensed signal and extracting a detected signal, said detected signal exhibiting a residual modulation thereupon at said second frequency only when there is optical absorption of the constituent in the measurement cell; and synchronous detection means for demodulating said second frequency from said detected signal so as to extract a DC signal, said DC signal being proportional to the absorption by the constituent in the measurement cell.

8. An apparatus according to claim 7 further comprising filtering means positioned ahead of said sensor means for passing only an ultranarrow range of wavelengths from each of said lightpaths to said sensor means.

9. An apparatus as in claim 8 further comprising means for tuning said filtering means so that said filtering means passes an ultranarrow range of wavelengths centered on an absorption line of the constituent in the measurement cell.

10. An apparatus as in claim 7 wherein said alternating means comprises a light reflecting chopper and said attenuating means comprise parallel plates of optical material.

11. An apparatus as in claim 10 wherein said reflecting chopper alternately passes said radiation directly through one of said paths and to a first 90° reflecting mirror and reflects said radiation in the other of said paths 90° to a second 90° reflecting mirror and from there to a third 90° reflecting mirror so that said radiation from both of said paths travels in parallel toward said sensor means.

12. An apparatus as in claim 7 further comprising calibration or calculation means for relating said DC signal from said synchronous detection means to the concentration of the constituent in the measurement cell.

13. An apparatus as in claim 7 further comprising means for thermally tufting said radiation means so that said radiation means emits a band of radiation centered on an absorption line of the constituent in the measurement cell.

14. An apparatus as in claim 7 wherein said detected signal also exhibits residual modulation when there is an imbalance in the relative power of light from said radiation means traversing said lightpaths, and said DC signal is an indication of said imbalance in the absence of optical absorption of the constituent in the measurement cell.

15. An apparatus as in claim 7 wherein said first frequency is above 8 MHz and said second frequency is below 2000 Hz.

16. An apparatus as in claim 7 further comprising a selectively connectable logarithmic circuit between said demodulating means and said synchronous detection means.

17. An apparatus for measuring optical absorption by a constituent gas in a measurement cell, said apparatus comprising:
radiation means for emitting broad band infrared radiation along one of a measurement lightpath and a reference lightpath, the measurement cell being positioned in said measurement lightpath so that said radiation passes therethrough;
modulating means for modulating said emitted radiation at a first frequency;
alternating means for alternately and periodically directing said radiation along one of said lightpaths at a second frequency;
attenuating means for balancing the relative power of said radiation in each of said lightpaths in the absence of optical absorption of the constituent in the measurement cell;
first and second sensor means for sensing radiation from each of said lightpaths and for producing a pair of sensed signals;
filtering means positioned ahead of said first and second sensor means for passing only an ultranarrow range of wavelengths from each of said lightpaths to said first sensor means and reflecting the remainder of said radiation band to said second sensor means;
demodulating means for demodulating said first frequency from said pair of sensed signals and extracting a pair of detected signals, said pair of detected signals exhibiting a residual modulation thereupon at said second frequency only when there is optical absorption of the constituent in the measurement cell; and
synchronous detection means for demodulating said second frequency from each of said pair of detected signals so as to extract a pair of DC signals, the one of said DC signals from said first sensor means being proportional to the optical absorption of the constituent in the measurement cell and the other of said DC signals from said second sensor means being proportional to any broad band absorption in the measurement cell.

18. An apparatus as in claim 17 further comprising means for tuning said filtering means so that said filtering means passes an ultranarrow range of wavelengths centered on an absorption line of the constituent in the measurement cell.

19. An apparatus as in claim 18 further comprising means for thermally tuning said radiation means so that said radiation means emits a band of radiation centered on an absorption line of the constituent in the measurement cell.

20. An apparatus as in claim 17 further comprising calibration or calculation means for relating said DC signal of said synchronous detection means to the concentration of the constituent in the measurement cell.

21. An apparatus as in claim 17 wherein said pair of detected signals also exhibit residual modulation when there is an imbalance in the relative power of light traversing said lightpaths and either of said pair of DC signals is an indication of said imbalance in the absence of optical absorption of the constituent in the measurement cell.

22. An apparatus for measuring optical absorption by a constituent gas in a measurement cell, said apparatus comprising:
radiation means for emitting broad band infrared radiation along a measurement lightpath, the measurement cell being positioned in said lightpath so that said radiation passes therethrough;
modulating means for modulating said emitted radiation at a predetermined frequency;
filtering means positioned behind the measurement cell for optically splitting said radiation into an absorption channel and a reference channel, said absorption channel having only an ultranarrow range of wavelengths from said lightpath, said reference channel having the remainder of said radiation band;
a first sensor means for sensing radiation in said absorption channel and for producing a first sensed signal;

a second sensor means for sensing radiation in said reference channel and producing a second sensed signal;

attenuating means disposed in one of said absorption and reference channels for balancing the relative power of light therein in the absence of optical absorption of the constituent in the measurement cell;

demodulating means for demodulating said predetermined frequency from each of said first and second sensed signals and extracting a respective pair of detected signals;

analog-to-digital convertor means for converting said pair of detected signals to a respective pair of digital detected signals; and a digital differential amplifier having a pair of differential inputs connected to said pair of digital detected signals and having an output proportional to the optical absorption of the constituent in the measurement cell.

23. An apparatus as in claim 22 further comprising means for tuning said filtering means so that said filtering means passes an ultranarrow range of wavelengths centered on an absorption line of the constituent in the measurement cell.

24. An apparatus as in claim 23 further comprising means for thermally tuning said radiation means so that said radiation means emits a band of radiation centered on an absorption line of the constituent in the measurement cell.

25. An apparatus as in claim 22 further comprising calibration or calculation means for relating said DC signal of said synchronous detection means to the concentration of the constituent in the measurement cell.

26. An apparatus as in claim 22 further comprising digital signal processing means connected between said analog-to-digital convertors and said digital differential amplifier.

27. An apparatus as in claim 22 wherein said predetermined frequency is above 8 MHz.

28. An apparatus as in claim 22 wherein said attenuating means comprise parallel plates of optical material.

29. An apparatus as in claim 22 wherein said first and second sensor means operate continuously and contemporaneously so that said digital differential amplifier provides a continuous concentration measurement.

30. An apparatus for measuring optical absorption by a constituent gas in a measurement cell, said apparatus comprising:

radiation means for emitting broad band infrared radiation along a measurement lightpath, the measurement cell being positioned in said lightpath so that said radiation passes therethrough;

sensor means for sensing radiation from said lightpath and for producing a sensed signal;

filtering means positioned ahead of said sensor means for passing only an ultranarrow range of wavelengths, the relative angle of said filtering means with respect to said lightpath influencing which ultranarrow range of wavelengths is passed by said filtering means;

vacillating means for alternately and periodically positioning said filtering means at an angle of one of $\theta$ and $\theta \pm \Delta\theta$ degrees with respect to said lightpath, said vacillating means vacillating at one predetermined frequency;

said filtering means passing wavelengths centered on $\lambda_A$ when said filtering means is positioned at $\theta$ degrees and passing wavelengths centered on $\lambda_B$ when said filtering means is positioned at $\theta \pm \Delta\theta$ degrees, $\Delta\theta$ being chosen so that only one of $\lambda_A$ and $\lambda_B$ is centered on an optical absorption line of the constituent in the measurement cell; and synchronous detection means for demodulating said one predetermined frequency from said sensed signal so as to extract a DC signal, said DC signal being proportional to the optical absorption of the constituent in the measurement cell.

31. An apparatus according to claim 30 wherein said DC signal is proportional to the optical absorption power differential between $\lambda_A$ and $\lambda_B$.

32. An apparatus according to claim 30 wherein said vacillating means is a cam, said cam having one surface for positioning said filtering means at an angle $\theta$ with respect to said lightpath and another surface for positioning said filtering means at an angle $\theta \pm \Delta\theta$ with respect to said lightpath.

33. An apparatus as in claim 30 further comprising means for thermally tuning said radiation means so that said radiation means emits equal energy at each of $\lambda_A$ and $\lambda_B$ and so that said DC signal from said synchronous detection means is zero in the absence of optical absorption of the constituent in the measurement cell.

34. An apparatus as in claim 30 further comprising means for tuning said filtering means so that said filtering means passes an ultranarrow range of wavelengths centered on an absorption line of the constituent in the measurement cell.

35. An apparatus according to claim 30 further comprising modulating means for modulating said emitted radiation at another predetermined frequency and demodulating means connected between said sensor means and said synchronous detection means for demodulating said another predetermined frequency from said sensed signal.

36. An apparatus as in claim 30 further comprising calibration or calculation means for relating said DC signal of said synchronous detection means to the concentration of the constituent in the measurement cell.

* * * * *